United States Patent [19]

Oyamada et al.

[11] 4,406,687

[45] Sep. 27, 1983

[54] USE OF ISOUREA DERIVATIVES AND TRIAZINE DERIVATIVES IN COMBINATION WITH GIBBERELLINS AS PLANT GROWTH REGULATORS

[75] Inventors: Kozo Oyamada; Takashi Matsui; Junzo Tobitsuka, all of Hiromachi; Yoshio Yamazaki; Masami Ogawa, both of Yasumachi, all of Japan

[73] Assignee: Sankyo Company Limited, Tokyo, Japan

[21] Appl. No.: 292,041

[22] Filed: Aug. 11, 1981

Related U.S. Application Data

[60] Division of Ser. No. 67,147, Aug. 16, 1979, Pat. No. 4,303,440, which is a continuation of Ser. No. 891,027, Mar. 28, 1978, Pat. No. 4,211,550, which is a continuation of Ser. No. 703,963, Jul. 9, 1976, abandoned.

[30] Foreign Application Priority Data

Jul. 16, 1971 [JP] Japan ................................. 46-87030
Sep. 5, 1975 [JP] Japan .............................. 50-107823
Sep. 22, 1975 [JP] Japan .............................. 50-114473

[51] Int. Cl.³ .................. A01N 9/12; A01N 9/22
[52] U.S. Cl. ............................. 71/89; 71/98; 71/93; 71/106; 71/111; 71/77
[58] Field of Search .............. 71/112, 89, 98, 93, 71/106, 77, 111

[56] References Cited

U.S. PATENT DOCUMENTS 3,100,149  8/1963  Ruge .................................... 71/89
3,118,753  1/1964  Shive ................................... 71/89
3,556,766  1/1971  Mitchell ............................... 71/89
3,989,501  11/1976 Kuratlo ................................ 71/93

Primary Examiner—James H. Reamer
Attorney, Agent, or Firm—Toren, McGeady and Stanger

[57] ABSTRACT 1-(hydrocarbylcarbamoyl)-3-(carboxy or hydrocarbyloxycarbonyl)-isoureas and isothioureas and the lactams of the 3-carboxy compounds are useful, in association with a gibberellin (which may be naturally present in a plant), as plant growth regulators.

11 Claims, No Drawings

USE OF ISOUREA DERIVATIVES AND TRIAZINE DERIVATIVES IN COMBINATION WITH GIBBERELLINS AS PLANT GROWTH REGULATORS

BACKGROUND OF THE INVENTION

This is a division of application Ser. No. 067,147, filed Aug. 16, 1979 now U.S. Pat. No. 4,303,440, which, in turn is a continuation of application Ser. No. 891,027, filed Mar. 28, 1978 now U.S. Pat. No. 4,211,550, which, in turn, is a continuation of application Ser. No. 703,963, filed July 9, 1976 now abandoned.

The present invention relates to a novel composition for plant growth regulation and specifically provides certain 1-(hydrocarbylcarbamoyl)-3-(carboxy or hydrocarbyloxycarbonyl)-isoureas and isothioureas and the lactams of the 3-carboxy compounds (which are triazine derivatives) for use in association with one or more gibberellins for the regulation of plant growth.

"Gibberellin" is a generic name for a series of natural plant hormones which act as accelerators of the growth of higher plants. The gibberellins were first discovered as the metabolic products of the soil-borne fungus, *Gibberella fujikuroi*, which causes a disease of rice seedlings manifested in the tall growth of infected plants. A series of related compounds identified as gibberellin $A_1$ through $A_{44}$ has been discovered and the various compounds isolated; the gibberellins have been found in the culture broth of *Gibberella fujikuroi* and in various higher plants including certain beans. At present the gibberellins are used for the acceleration or regulation of various stages of plant development, particularly growth, efflorescence, germination and parthenocarpy, particularly of the true grasses of the order Gramineae, flowering plants, vegetables, fruit trees and other trees. The main component of the gibberellins used in practice is gibberellin $A_3$, otherwise known as gibberellic acid.

The gibberellins have, therefore, a variety of useful functions. However, their use is greatly limited by their expense and insufficient effectiveness at low concentrations. As a result, research has concentrated on an effort to find a synergistic agent which can be used to enhance the activity of the gibberellins. Few synergistic agents have, however, been discovered and fewer still have been put to practical use.

There is, therefore, an urgent need for synergistic agents for use with the gibberellins.

BRIEF SUMMARY OF INVENTION

It is an object of the present invention to provide new synergistic agents for use with the gibberellins in the regulation of plant growth, these synergistic agents being the 1-(hydrocarbylcarbamoyl)-3-(carboxy or hydrocarbyloxycarbonyl)-isoureas and isothioureas and the lactams of the 3-carboxy compounds.

It is a further object of the invention to provide a composition for plant growth regulation comprising a gibberellin and one or more of the synergistic agents of the invention.

It is a yet further object of the invention to provide a method of regulating plant growth by the administration of one or more of the synergistic agents of the invention in association with gibberellin, which may be provided naturally by the plant being treated.

The synergistic agents of the present invention are compounds having the formula (I):

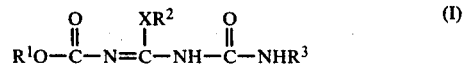

[wherein:
- $R^1$ represents a hydrogen atom or a lower alkyl group, a lower alkenyl group, a lower alkynyl group or a phenyl group;
- $R^2$ represents a lower alkyl group, a lower alkenyl group, a lower alkynyl group or a benzyl group;
- $R^3$ represents a lower alkyl group, a cyclohexyl group or a group of the formula:

(in which $R^4$ represents a lower alkyl group, a lower alkoxy group or a halogen atom and n is 0, 1, 2 or 3); and
- X represents an oxygen or a sulphur atom] and the lactams of the above compounds wherein $R^1$ represents a hydrogen atom, i.e. those triazine derivatives of formula (II):

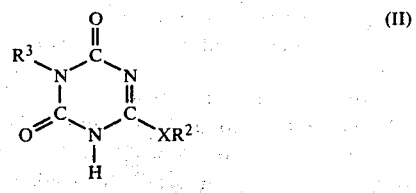

and salts and alcohol adducts of said lactams.

The administration of one or more of the synergistic agents of the invention in association with a gibberellin enables the amount of gibberellin used to be reduced and the acceleration or regulation of growth, efflorescence, germination or parthenocarpy of the plant to be treated to be greatly enhanced. The combined use of one or more of the synergistic agents of the invention in association with one or more gibberellins in particular has a remarkable effect on plant growth. Where gibberellins are produced naturally by the plant to be treated, the administration of additional gibberellin may be reduced or even omitted altogether, depending upon the amount of gibberellin produced by the plant. Where no or almost no gibberellin is produced by the plant, the synergistic agents of the invention are used in association with additional gibberellin. Even if a very small quantity of a gibberellin is present, its activity can be greatly enhanced by the administration of the synergistic agents of the invention.

DETAILED DESCRIPTION OF INVENTION

The compounds of formula (I) can exist in the following tautomeric forms:

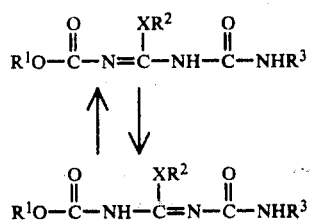

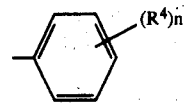

(in which $R^1$, $R^2$, $R^3$ and X are as defined above) and both forms are of use in the present invention.

When $R^1$ in the compounds of formula (I) represents a lower alkyl group, it preferably represents a straight chain or branched chain lower alkyl group having from 1 to 6 carbon atoms, more preferably from 1 to 4 carbon atoms, for example methyl, ethyl, propyl, isopropyl, butyl, isobutyl, sec-butyl, t-butyl, pentyl, isopentyl, sec-pentyl, 2-methylbutyl, t-pentyl, hexyl, 2-hexyl, 2-methylpentyl, 3-methylpentyl, 4-methylpentyl, 3-hexyl, 2-ethylbutyl, 2-methyl-2-pentyl or 2,2-dimethylbutyl. When $R^1$ represents a lower alkenyl group, it preferably represents a straight chain or branched chain lower alkenyl group having from 3 to 6 carbon atoms, more preferably 3 or 4 carbon atoms, for example allyl, 2-butenyl, 1-methyl-2-propenyl, 2-methyl-2-propenyl, 1-methyl-2-butenyl, 2-methyl-2-butenyl, 3-butenyl, 1-methyl-3-butenyl, 2-methyl-3-butenyl, 3-methyl-2-butenyl, 3-pentenyl, 2-hexenyl, 3-hexenyl or 4-hexenyl. When $R^1$ represents a lower alkynyl group, it preferably represents a straight chain or branched chain alkynyl group having from 3 to 6 carbon atoms, more preferably 3 or 4 carbon atoms, for example 2-propynyl, 2-butynyl or 2-methyl-3-butyn-2-yl. Alternatively, $R^1$ may represent a phenyl group.

When $R^2$ in compounds of formulae (I) and (II) represents a lower alkyl group, it preferably represents a straight chain or branched chain alkyl group having from 1 to 6 carbon atoms, more preferably from 1 to 4 carbon atoms and most preferably from 1 to 3 carbon atoms, for example, methyl, ethyl, propyl, isopropyl, butyl, isobutyl, sec-butyl, t-butyl, pentyl, isopentyl, sec-pentyl, 2-methylbutyl, t-pentyl, hexyl, 2-hexyl, 2-methylpentyl, 3-methylpentyl, 4-methylpentyl, 3-hexyl, 2-ethylbutyl, 2-methyl-2-pentyl or 2,2-dimethylbutyl. When $R^2$ represents a lower alkenyl group, it preferably represents a straight chain or branched chain lower alkenyl group having from 3 to 6 carbon atoms, more preferably 3 or 4 carbon atoms, for example allyl, 2-butenyl, 1-methyl-2-propenyl, 2-methyl-2-propenyl, 1-methyl-2-butenyl, 2-methyl-2-butenyl, 3-butenyl, 1-methyl-3-butenyl, 2-methyl-3-butenyl, 3-pentenyl, 2-hexenyl, 3-hexenyl or 4-hexenyl. When $R^2$ represents a lower alkynyl group, it preferably represents a straight chain or branched chain lower alkynyl group having from 3 to 6 carbon atoms, more preferably 3 or 4 carbon atoms, for example 2-propynyl, 2-butynyl or 2-methyl-3-butyn-2-yl. Alternatively, $R^2$ may represent a benzyl group.

When $R^3$ represents a lower alkyl group, it preferably represents a lower alkyl group having from 1 to 6 carbon atoms, more preferably from 1 to 4 carbon atoms, for example methyl, ethyl, propyl, isopropyl, butyl, isobutyl, sec-butyl, t-butyl, pentyl, isopentyl, sec-pentyl, 2-methylbutyl, t-phentyl, hexyl, 2-hexyl, 2-methylpentyl, 3-methylpentyl, 4-methylpentyl, 3-hexyl, 2-ethylbu-tyl, 2-methyl-2-pentyl or 2,2-dimethylbutyl. When $R^3$ represents a group of formula

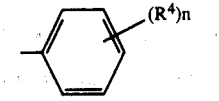

$R^4$ preferably represents: a straight chain or branched chain lower alkyl group having from 1 to 4 carbon atoms, more preferably from 1 to 3 carbon atoms, for example methyl, ethyl, propyl, isopropyl, butyl, isobutyl, sec-butyl or t-butyl, most preferably methyl or ethyl; a straight chain or branched chain lower alkoxy group preferably having from 1 to 3 carbon atoms, for example methoxy, ethoxy, propoxy or isopropoxy, most preferably methoxy; or a halogen atom, such as chlorine, bromine, fluorine or iodine, preferably a chlorine atom; and n is 0, 1, 2 or 3, preferably 1 or 2. When n is 2 or 3, the groups $R^4$ may be the same or different.

X represents an oxygen atom or a sulphur atom, and preferably represents an oxygen atom in the compounds of formula (I) where $R^4$ represents a substituted or unsubstituted phenyl group and in lactams of formula (II), and preferably represents a sulphur atom in the compounds of formula (I) where $R^3$ represents a lower alkyl group or cyclohexyl group.

Particularly preferred synergistic agents of the present invention having outstanding synergistic activity are those in which:

$R^1$ represents a straight chain or branched chain lower alkyl group having from 1 to 4 carbon atoms, preferably methyl, ethyl or isopropyl; a straight chain or branched chain lower alkenyl group having 3 or 4 carbon atoms, preferably allyl; or a straight chain or branched chain alkynyl group having 3 or 4 carbon atoms, preferably 2-propynyl;

$R^2$ represents a straight chain or branched chain lower alkyl group having from 1 to 4 more preferably from 1 to 3 carbon atoms, preferably methyl or ethyl; a straight chain or branched chain lower alkenyl group having 3 or 4 carbon atoms, preferably allyl; or a straight chain or branched chain lower alkynyl group having 3 or 4 carbon atoms, preferably 2-propynyl; and $R^3$ represents a straight chain or branched chain alkyl group having from 3 to 6 carbon atoms, preferably isopropyl, or a group of formula

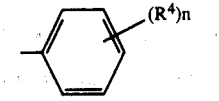

in which $R^4$ represents a methyl, methoxy or halogen (preferably chlorine) atom; in particular the substitutent $R^4$ is preferably in the ortho or para position of the phenyl group and thus $R^3$ most preferably represents a p-chlorophenyl, p-bromophenyl, p-iodophenyl, p-methylphenyl, p-ethylphenyl, 2,4-dichlorophenyl, 2,4-dimethylphenyl or 4-chloro-2-methylphenyl group.

It is also possible to use salts and alcohol adducts of the synergistic agents of the invention, particularly the lactams of formula (II). These compounds can exist as anions by releasing an $H^+$ ion in the presence of a base and will thus form various salts with positive ions, particularly metal ions, such as sodium, potassium, calcium, magnesium, iron, aluminium, manganese or copper, or will form H+-addition salts with organic bases, for example trimethylamine, triethylamine, ethanolamine or isopropylamine.

The alcohol adducts are new compounds. Compounds of formula (II) in which $R^3$ represents a phenyl group having substituents at the 2- and 4-positions will form a 1:1 adduct with alcohols such as methanol and ethanol. These salts and alcohol adducts can also be used advantageously as synergistic agents in accordance with the present invention.

Following Table I is a non-limiting list of individual compounds of formula (I). The numbers appended to the compounds in the list will be used to identify them hereinafter.

TABLE I

| Compd. No. | X | $R^1$ | $R^2$ | $R^3$ | Melting point (°C.) or Refractive Index |
|---|---|---|---|---|---|
| 1 | O | $CH_3$ | $CH_3$ | —⟨C₆H₄⟩—$CH_3$ | m.p. 169–170 |
| 2 | O | $CH_3$ | $C_2H_5$ | " | m.p. 155–156 |
| 3 | O | $C_2H_5$ | $CH_3$ | " | m.p. 146–148 |
| 4 | O | $(CH_3)_2CH$— | $C_2H_5$ | " | m.p. 107–108 |
| 5 | O | $CH_3$ | $CH_2=CH—CH_2$— | " | m.p. 126–127 |
| 6 | O | $CH_2=CH—CH_2$— | $CH_3$ | " | m.p. 146–147 |
| 7 | O | $C_2H_5$ | $(CH_3)_2CHCH_2$— | " | m.p. 101–102 |
| 8 | O | $(CH_3)_2CHCH_2$— | $(CH_3)_2CHCH_2$— | " | m.p. 97–98 |
| 9 | O | $CH_3$ | —⟨C₆H₅⟩—$CH_2$— | " | m.p. 127–128 |
| 10 | O | $C_2H_5$ | $C_2H_5$ | " | m.p. 141–143 |
| 11 | O | $CH≡C—CH_2$— | $C_2H_5$ | " | m.p. 116–118 |
| 12 | O | $CH_3$ | $CH_3$ | —⟨C₆H₄⟩—Cl | m.p. 173–175 |
| 13 | O | $CH_3$ | $C_2H_5$ | " | m.p. 169–170 |
| 14 | O | $C_2H_5$ | $CH_3$ | " | m.p. 160–161 |
| 15 | O | $C_2H_5$ | $C_2H_5$ | " | m.p. 151–152 |
| 16 | O | $(CH_3)_2CH$— | $C_2H_5$ | " | m.p. 136–137 |
| 17 | O | $CH_2=CH—CH_2$— | $CH_3$ | " | m.p. 149–150 |
| 18 | O | $CH_3$ | $CH_2=CH—CH_2$— | " | m.p. 144–145 |
| 19 | O | $CH≡C—CH_2$— | $C_2H_5$ | " | m.p. 138–140 |
| 20 | O | $C_2H_5$ | $(CH_3)_2CHCH_2$— | " | m.p. 110–111 |
| 21 | O | $(CH_3)_2CHCH_2$— | $(CH_3)_2CHCH_2$— | " | m.p. 132–133 |
| 22 | O | $CH_3$ | $C_2H_5$ | —⟨C₆H₅⟩ | m.p. 145–146 |
| 23 | O | $CH_3$ | $C_2H_5$ | —⟨C₆H₄⟩ (Cl ortho) | m.p. 79–80 |
| 24 | O | $CH_3$ | $C_2H_5$ | —⟨C₆H₄⟩ (Cl) | m.p. 128–129 |

TABLE I-continued
| Compd. No. | X | R¹ | R² | R³ | Melting point (°C.) or Refractive Index |
|---|---|---|---|---|---|
| 25 | O | CH₃ | C₂H₅ | 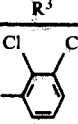 | m.p. 97–98 |
| 26 | O | CH₃ | C₂H₅ | 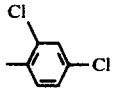 | m.p. 92–93 |
| 27 | O | CH₃ | C₂H₅ | 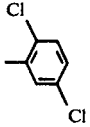 | m.p. 118–119 |
| 28 | O | CH₃ | C₂H₅ | 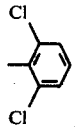 | m.p. 143–144 |
| 29 | O | CH₃ | C₂H₅ | 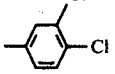 | m.p. 159–160 |
| 30 | O | CH₃ | C₂H₅ | 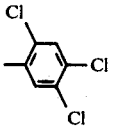 | m.p. 141–142 |
| 31 | O | CH₃ | C₂H₅ | 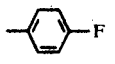 | m.p. 177–178 |
| 32 | O | CH₃ | C₂H₅ | 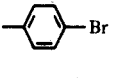 | m.p. 176–177 |
| 33 | O | CH₃ | C₂H₅ | 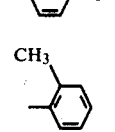 | m.p. 180–181 |
| 34 | O | CH₃ | C₂H₅ |  | m.p. 73–74 |
| 35 | O | CH₃ | C₂H₅ |  | m.p. 127–128 |
| 36 | O | CH₃ | C₂H₅ | 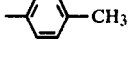 | m.p. 102–103 |
| 37 | O | CH₃ | C₂H₅ | 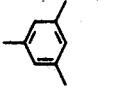 | m.p. 116–118 |
| 38 | O | CH₃ | C₂H₅ | 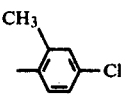 | m.p. 109–110 |

TABLE I-continued

| Compd. No. | X | R¹ | R² | R³ | Melting point (°C.) or Refractive Index |
|---|---|---|---|---|---|
| 39 | O | $CH_3$ | $C_2H_5$ | 2-CH₃, 3-Cl phenyl | m.p. 89–90 |
| 40 | O | $CH_3$ | $C_2H_5$ | 4-$C_2H_5$ phenyl | m.p. 125–126 |
| 41 | O | $CH_3$ | $C_2H_5$ | 4-n-$C_3H_7$ phenyl | m.p. 114–115 |
| 42 | O | $CH_3$ | $C_2H_5$ | 4-$OCH_3$ phenyl | m.p. 153–155 |
| 43 | O | $CH_3$ | $CH_3$ | phenyl | m.p. 150–151 |
| 44 | O | $CH_3$ | $CH_3$ | 2-Cl phenyl | m.p. 95–97 |
| 45 | O | $CH_3$ | $CH_3$ | 2,4-di-Cl phenyl | m.p. 112–113 |
| 46 | O | $CH_3$ | $CH_3$ | 3,4-di-Cl phenyl | m.p. 178–179 |
| 47 | O | $CH_3$ | $CH_3$ | 4-F phenyl | m.p. 163–164 |
| 48 | O | $CH_3$ | $CH_3$ | 4-I phenyl | m.p. 175–176 |
| 49 | O | $CH_3$ | $CH_3$ | 3-$CH_3$ phenyl | m.p. 165–166 |
| 50 | O | $CH_3$ | $CH_3$ | 3,5-di-$CH_3$ phenyl | m.p. 145–146 |
| 51 | O | $CH_3$ | $CH_3$ | 2-$CH_3$, 4-Cl phenyl | m.p. 113–114 |
| 52 | O | $CH_3$ | $CH_3$ | 4-$C_2H_5$ phenyl | m.p. 131–135 |
| 53 | O | $CH_3$ | $CH_3$ | 4-n-$C_3H_7$ phenyl | m.p. 139–140 |
| 54 | S | $CH_3$ | $CH_3$ | 4-Cl phenyl | m.p. 171–172 |
| 55 | S | $CH_3$ | $CH_3$ | 4-$CH_3$ phenyl | m.p. 168–169 |

TABLE I-continued

| Compd. No. | X | R¹ | R² | R³ | Melting point (°C.) or Refractive Index |
|---|---|---|---|---|---|
| 56 | S | $CH_3$ | $CH_3$ | 4-$C_2H_5$-phenyl | m.p. 146–147 |
| 57 | S | $CH_3$ | $CH_3$ | 2,4-di-Cl-phenyl | m.p. 136–137 |
| 58 | S | $CH_3$ | $CH_3$ | 2-$CH_3$-4-Cl-phenyl | m.p. 140–141 |
| 59 | S | $CH_3$ | $CH_3$ | 2,6-di-Cl-phenyl | m.p. 128–129 |
| 60 | S | $CH_3$ | $CH_3$ | 2,4-di-$CH_3$-phenyl | m.p. 120–121 |
| 61 | S | $CH_3$ | $CH_3$ | 3,4-di-Cl-phenyl | m.p. 151–152 |
| 62 | S | $CH_3$ | $CH_3$ | 3,4,5-tri-Cl-phenyl | m.p. 199–200 |
| 63 | S | $CH_3$ | $C_2H_5$ | 2,4-di-Cl-phenyl | m.p. 89–92 |
| 64 | S | $CH_3$ | $C_2H_5$ | 4-$CH_3$-phenyl | m.p. 132–134 |
| 65 | S | $CH_3$ | $CH_2=CH-CH_2-$ | 2,4-di-Cl-phenyl | m.p. 112–114 |
| 66 | S | $CH_3$ | $CH_3=CH-CH_2-$ | 4-$CH_3$-phenyl | m.p. 103–105 |
| 67 | S | $CH_3$ | $HC\equiv C-CH_2-$ | 2,4-di-Cl-phenyl | m.p. 171–172 |
| 68 | S | $CH_3$ | $HC\equiv C-CH_2-$ | 4-$CH_3$-phenyl | m.p. 161–162 |
| 69 | S | $C_2H_5$ | $CH_3$ | phenyl | m.p. 105–109 |
| 70 | S | $C_2H_5$ | $CH_3$ | 4-Cl-phenyl | m.p. 126–129 |
| 71 | S | $C_2H_5$ | $CH_3$ | 4-$CH_3$-phenyl | m.p. 126–130 |

TABLE I-continued

| Compd. No. | X | R¹ | R² | R³ | Melting point (°C.) or Refractive Index |
|---|---|---|---|---|---|
| 72 | S | $C_2H_5$ | $C_2H_5$ | 4-methylphenyl ($-C_6H_4-CH_3$) | m.p. 110–112 |
| 73 | S | $CH_3$ | $HC\equiv C-CH_2-$ | 4-chlorophenyl ($-C_6H_4-Cl$) | m.p. 169–170 |
| 74 | S | $CH_3$ | $CH_3$ | $CH_3$ | m.p. 134–136 |
| 75 | S | $CH_3$ | $CH_3$ | $(CH_3)_2CH-$ | m.p. 136–137 |
| 76 | S | $CH_3$ | $C_2H_5$ | $(CH_3)_3C-$ | m.p. 83–84 |
| 77 | S | $C_2H_5$ | $CH_3$ | $CH_3$ | m.p. 97–99 |
| 78 | S | $C_2H_5$ | $CH_3$ | $C_2H_5$ | m.p. 43–46 |
| 79 | S | $C_2H_5$ | $CH_3$ | $n\text{-}C_3H_7$ | m.p. 36–41 |
| 80 | S | $C_2H_5$ | $CH_3$ | $(CH_3)_2CH-$ | m.p. 95–97 |
| 81 | S | $C_2H_5$ | $CH_3$ | $n\text{-}C_4H_9$ | m.p. 42–44 |
| 82 | S | $C_2H_5$ | $CH_3$ | $(CH_3)_3C-$ | m.p. 50–54 |
| 83 | S | $C_2H_5$ | $CH_3$ | cyclohexyl | m.p. 118–119 |
| 84 | S | $CH_3$ | $-CH_2CH=CH_2$ | $(CH_3)_2CH-$ | m.p. 103–106 |
| 85 | S | $CH_3$ | $-CH_2C\equiv CH$ | $(CH_3)_2CH-$ | m.p. 119–120 |
| 86 | O | $CH_3$ | $C_2H_5$ | $CH_3$ | m.p. 92–94 |
| 87 | O | $CH_3$ | $C_2H_5$ | cyclohexyl | m.p. 87–88 |
| 88 | O | $C_2H_5$ | $C_2H_5$ | $CH_3$ | m.p. 60–62 |
| 89 | O | $C_2H_5$ | $C_2H_5$ | cyclohexyl | m.p. 78–79 |
| 90 | O | $C_2H_5$ | $(CH_3)_2CHCH_2-$ | cyclohexyl | m.p. 57–58 |
| 91 | O | $C_2H_5$ | $CH_3$ | $CH_3$ | m.p. 72–73 |
| 92 | O | $CH_3$ | $C_2H_5$ | $(CH_3)_2CH-$ | $n_D^{25}$ 1.4709 |
| 93 | O | $CH_3$ | $C_2H_5$ | $C_2H_5$ | $n_D^{25}$ 1.4727 |
| 94 | O | $CH_3$ | $C_2H_5$ | $n\text{-}C_4H_9$ | $n_D^{25}$ 1.4712 |
| 95 | O | $CH_3$ | $C_2H_5$ | $n\text{-}C_3H_7$ | $n_D^{25}$ 1.4721 |
| 96 | S | $CH_3$ | $-CH_2-C_6H_5$ | $(CH_3)_2CH-$ | m.p. 101–103 |
| 97 | O | $CH\equiv C-CH_2-$ | $C_2H_5$ | $CH_3$ | m.p. 133–137 |
| 98 | S | phenyl | $CH_3$ | 4-chlorophenyl ($Cl-C_6H_4-$) | m.p. 286 (decomp.) |
| 99 | S | phenyl | $CH_3$ | 4-methylphenyl ($CH_3-C_6H_4-$) | m.p. 151–152 |

TABLE I-continued

| Compd. No. | X | R¹ | R² | R³ | Melting point (°C.) or Refractive Index |
|---|---|---|---|---|---|
| 100 | S | CH≡C—CH₂— | CH₃ | Cl—C₆H₄— | m.p. 126–129 |
| 101 | S | CH≡C—CH₂— | CH₃ | 2,3-Cl₂—C₆H₃— | m.p. 146–148 |
| 102 | S | CH≡C—CH₂— | CH₃ | CH₃—C₆H₄— | m.p. 137–140 |
| 103 | S | CH≡C—CH₂— | CH₃ | (CH₃)₂CH— | m.p. 88–90 |
| 104 | S | CH≡C—CH₂— | CH₃ | C₆H₁₁— | m.p. 124–126 |
| 105 | S | CH≡C—CH₂— | CH₂=CH—CH₂— | Cl—C₆H₄— | m.p. 111–113 |

Following Table II gives a non-limiting list of individual lactams of formula (II). The numbers appended to the lactams in the list will be used to identify them hereinafter.

TABLE II

| Compd. No. | X | R² | R³ | Adduct or Salt | Melting point (°C.) |
|---|---|---|---|---|---|
| 106 | O | $C_2H_5$ | C₆H₅— | — | 257–258 |
| 107 | O | $C_2H_5$ | CH₃—C₆H₄— | — | 260–262 |
| 108 | O | $C_2H_5$ | Cl—C₆H₄— | — | about 257 |
| 109 | O | $C_2H_5$ | 2,3-Cl₂—C₆H₃— | methanol adduct | 125–128 |
| 110 | O | $C_2H_5$ | 2,4-Cl₂—C₆H₃— | ethanol adduct | 120–124 |
| 111 | O | $C_2H_5$ | 2,3-Cl₂—C₆H₃— | — | 267–268 |
| 112 | O | $C_2H_5$ | 2,4,5-Cl₃—C₆H₂— | — | 217–222 |
| 113 | O | $C_2H_5$ | 4-Cl-2-CH₃—C₆H₃— | ethanol adduct | 100–105 |

TABLE II-continued

| Compd. No. | X | R² | R³ | Adduct or Salt | Melting point (°C.) |
|---|---|---|---|---|---|
| 114 | O | C₂H₅ | 2,5-(CH₃)₂-C₆H₃- | — | 201—203 |
| 115 | O | C₂H₅ | 2,6-Cl₂-C₆H₃- | — | about 220 |
| 116 | O | (CH₃)₂CH— | 4-CH₃-C₆H₄- | — | 218–219 |
| 117 | O | (CH₃)₂CH— | 4-Cl-C₆H₄- | — | 220–222 |
| 118 | O | C₂H₅ | 2-Cl-C₆H₄- | — | 214–215 |
| 119 | O | —CH₂—C₆H₅ | 3,4-Cl₂-C₆H₃- | — | 241 |
| 120 | O | —CH₂CH=CH₂ | 4-CH₃-C₆H₄- | — | 189–191 |
| 121 | S | CH₃ | C₆H₅- | — | about 265 |
| 122 | S | CH₃ | 4-CH₃-C₆H₄- | — | 275–276 |
| 123 | S | CH₃ | 4-Cl-C₆H₄- | — | (decomp.) 287–288 |
| 124 | S | CH₃ | 4-C₂H₅-C₆H₄- | — | (decomp.) 247–248 |
| 125 | S | CH₃ | 2,4-Cl₂-C₆H₃- | — | 240–242 |
| 126 | S | CH₃ | 2,6-Cl₂-C₆H₃- | — | 282–284 |
| 127 | S | CH₃ | 4-Cl-2-CH₃-C₆H₃- | — | 297–298 |
| 128 | S | CH₃ | 2,5-(CH₃)₂-C₆H₃- | — | 242–244 |

TABLE II-continued

| Compd. No. | X | R² | R³ | Adduct or Salt | Melting point (°C.) |
|---|---|---|---|---|---|
| 129 | S | CH₃ | 2,4,6-trichlorophenyl | — | 252–253 |
| 130 | S | C₂H₅ | 4-CH₃-phenyl | — | 223–226 |
| 131 | S | —CH₂CH=CH₂ | 4-CH₃-phenyl | — | 236–237 |
| 132 | S | CH₃ | (CH₃)₂CH— | — | 191–192 |
| 133 | O | CH₃ | 4-CH₃-phenyl | sodium salt | >280 |
| 134 | O | C₂H₅ | 4-CH₃O-phenyl | — | m.p. 248–249 |

Of the compounds listed above, the preferred compounds are Compounds Nos. 1, 2, 3, 4, 5, 6, 7, 8, 10, 11, 12, 13, 14, 15, 16, 17, 18, 19, 20, 26, 31, 32, 33, 38, 40, 42, 45, 47, 48, 51, 52, 54, 55, 56, 57, 58, 63, 64, 65, 66, 68, 70, 71, 73, 75, 80, 92, 107, 108, 109, 110, 113, 114, 116, 117, 120, 122, 123, 124, 125, 127, 128, 130, 131, 132 and 133. The most preferred compounds are Compounds No. 1, 2, 3, 4, 5, 6, 10, 11, 12, 13, 14, 15, 16, 17, 19, 26, 32, 38, 40, 45, 51, 52, 54, 55, 70, 71, 107, 108, 109, 110, 113, 116, 117, 120, 122, 123, 128 and 133.

Of the compounds listed in the above Table, Compounds Nos. 1 to 22, 24, 27, 29, 34, 45, 54, 75, 80, 86 to 91, 108, 109, 110, 113, 121, 123, 127, and 133 are known and proposed as herbicides. The novel compounds may be synthesized by processes analogous to those employed for preparing the known compounds. For example, Compounds 1 to 53, 86 to 95 and 97 can be prepared by the method described in Japanese Patent Provisional Publication No. 49-25133 (1974). Compounds 54 to 85 and 96 can be synthesized starting from pseudothiourea by the method described in Japanese Patent Provisional Publication No. 49-102839 (1974). Since, however, pseudothiourea tends to cause side reactions, thioallophanic acid or an ester thereof is preferably used in place of the pseudothiourea, giving the desired compound in good yield by a convenient reaction, which may be represented as follows:

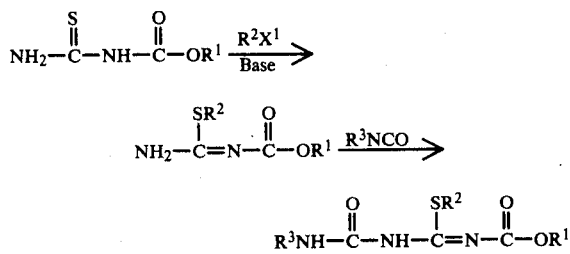

(in which R¹, R² and R³ are as defined above and X' represents a halogen atom, a sulphonic acid residue or a phosphoric acid residue).

The lactams of formula (II) may be prepared by the process described in Japanese Patent Provisional Publication No. 48-36341 (1973), which proposes the use of certain of the lactams (II) as herbicides.

The preparation of the synergistic agents of the invention is illustrated by the following non-limiting Examples.

EXAMPLE 1

1-(2,4-dichlorophenylcarbamoyl)-2-ethyl-3-methoxycarbonylisourea (Compound 26)

2 g of 2-ethyl-1-methoxycarbonylisourea [prepared as described in Japanese Patent Provisional Publication No. 49-25133 (1974)] and 1.88 g of 2,4-dichlorophenyl isocyanate were dissolved in 100 ml of benzene and the mixture was refluxed for 1 hour. The benzene was then removed by evaporation under reduced pressure and the residue was recrystallized from hexane, giving 2.7 g (yield 81%) of the desired compound as white needles melting at 92°–93° C.

EXAMPLE 2

1-(2,4-dichlorophenylcarbamoyl)-3-methoxycarbonyl-2-methylisothiourea (Compound 57)

1.34 g of methyl thioallophanate, 1.6 g of methyl iodide and 1.4 g of potassium carbonate were charged into 20 ml of acetone. The mixture was stirred at room temperature for about 10 hours, after which insoluble substances were removed by filtration. 1.88 g of 2,4-dichlorophenyl isocyanate were added to the filtrate and the mixture was refluxed for 1 hour. The solvent was then removed by evaporation under reduced pressure and the residue was recrystallized from methanol giving 2.6 g (yield 77%) of the desired compound in the form of white crystals melting at 136°–137° C.

EXAMPLE 3

1-(2,4-dichlorophenylcarbamoyl)-2-ethyl-3-methoxycarbonylisothiourea (Compound 63)

The procedure described in Example 2 was repeated, except that 1.3 g of ethyl bromide were used in place of the methyl iodide. 3.0 g (yield 82.4%) of the desired compound were obtained, in the form of white crystals melting at 89°–92° C.

EXAMPLE 4

2-allyl-3-methoxycarbonyl-1-(p-tolylcarbamoyl)-isothiourea (Compound 66)

The procedure described in Example 2 was repeated, except that 1.25 g of allyl bromide were used in place of the methyl iodide and 1.33 g of p-tolyl isocyanate were used in place of the 2,4-dichlorophenyl isocyanate. 2.4 g (yield 78.3%) of the desired compound were obtained in the form of colourless prisms having a melting point of 103°–105° C.

EXAMPLE 5

3-methoxycarbonyl-2-propargyl-1-(p-tolylcarbamoyl)-isothiourea (Compound 68)

The procedure described in Example 4 was repeated, except that 1.3 g of propargyl bromide were used in place of the allyl bromide. There were obtained 2.4 g (yield 79%) of the desired compound in the form of white needles having a melting point of 161°–162° C.

EXAMPLE 6

3-ethoxycarbonyl-2-ethyl-1-(p-tolylcarbamoyl)-isothiourea (Compound 72)

The procedure described in Example 2 was repeated, except that 1.48 g of ethyl thioallophanate were used in place of the methyl thioallophanate, 1.3 g of ethyl bromide were used in place of the methyl iodide and 1.33 g of p-tolyl isocyanate were used in place of the 2,4-dichlorophenyl isocyanate. 2.5 g (yield 81%) of the desired compound were obtained in the form of colourless prisms having a melting point of 110°–112° C.

EXAMPLE 7

3-methoxycarbonyl-2-methyl-1-methylcarbamoylisothiourea (Compound 74)

To 20 ml of acetone were added 1.34 g of methyl thioallophanate, 1.6 g of methyl iodide and 1.4 g of potassium carbonate. The mixture was stirred for about 10 hours at room temprature after which insoluble materials were removed by filtration. 0.6 g of methyl isocyanate was added to the filtrate. The mixture was then stood over night at room temperature, after which the solvent was removed by evaporation under reduced pressure. The residue was recrystallized from hexane, giving 1.1 g (yield 54%) of the desired compound in the form of white crystals melting at 134°–136° C.

EXAMPLE 8

2-allyl-1-isopropylcarbamoyl-3-methoxycarbonylisothiourea (Compound 84)

The procedure described in Example 7 was repeated, except that 1.25 g of allyl bromide were used in place of the methyl iodide and 0.9 g of isopropyl isocyanate was used in place of the methyl isocyanate. 1.22 g (yield 47.1%) of the desired compound were obtained in the form of colourless prisms having a melting point of 103°–106° C.

EXAMPLE 9

1-isopropylcarbamoyl-3-methoxycarbonyl-2-propargylisothiourea (Compound 85)

The procedure described in Example 8 was repeated, except that 1.3 g of propargyl bromide were used in place of the allyl bromide. 1.0 g (yield 39%) of the desired compound was obtained in the form of white needles melting at 119°–120° C.

EXAMPLE 10

Methanol adduct of 1-(2,4-dichlorophenyl)-1,3-dihydro-4-ethoxy-1,3,5-triazine-2,6-dione (Compound 109)

2 g of 2-ethyl-1-methoxycarbonylisourea [prepared as described in Japanese Patent Provisional Publication No. 49-2513 (1974)] and 1.9 g of 2,4-dichlorophenyl isocyanate were dissolved in 100 ml of benzene. The mixture was refluxed for 1 hour, after which the benzene was removed by evaporation under reduced pressure. 1.0 g of sodium methoxide and 20 ml of methanol were added to the residue and the mixture was refluxed for 3 hours. After cooling the mixture, 5 ml of 6 N hydrochloric acid were added and the mixture was extracted with 50 ml of chloroform. The solvent was then removed by evaporation under reduced pressure and the residue was recrystallized from methanol giving 2.2 g (yield 66%) of plate-like crystals melting at 125°–128° C.

Elemental Analysis: Calculated for $C_{12}H_{13}Cl_2N_3O_4$: C, 43.13%; H, 3.92%; N, 12.57%; Cl, 21.22%. Found: C, 42.70%; H, 3.79%; N, 12.63%; Cl, 21.39%.

EXAMPLE 11

Ethanol adduct of 1-(4-chloro-2-methylphenyl)-4-ethoxy-1,3-dihydro-1,3,5-triazine-2,6-dione (Compound 113)

The procedure described in Example 10 was repeated, except that 1.8 g of 4-chloro-2-methylphenyl isocyanate were used in place of the 2,4-dichlorophenyl isocyanate; the crystals thus obtained were recrystallized from ethanol, giving 2.0 g (yield 61%) of white crystal, melting at 100°–105° C.

Elemental Analysis: Calculated for $C_{14}H_{18}ClN_3O_4$: C, 51.30%; H, 5.54%; N, 12.82%; Cl, 10.82%. Found: C, 50.52%; H, 5.24%; N, 12.90%; Cl, 11.14%.

The compounds of the invention may be applied alone to plants which naturally produce a gibberellin but they are preferably applied in admixture with one or more of the gibberellins, preferably a naturally produced mixture of gibberellins. If desired, the compound or the composition comprising the compound and the gibberellin may be applied in admixture with a carrier or, if necessary, other auxiliary agents to form any one of the standard types of preparation commonly used in agriculture, for example, a dust, granules, grains, a wettable powder, an emulsion, an aqueous solution etc.

Suitable solid carriers are clay, talc, kaolin, bentonite, terra abla, calcium carbonate, diatomaceous earth, silica, synthetic calcium silicate etc.. Suitable liquid carriers are: aliphatic hydrocarbons, such as ligroin, kerosine, mineral oil etc.; aromatic hydrocarbons, such as benzene, toluene, xylene, methylnaphthalene etc.; chlorinated hydrocarbons, such as chloroform, dichloroethane etc.; alcohols, such as methanol, isopropanol, butanol etc.; ketones, such as acetone, methyl ethyl ketone, cyclohexanone etc.; and amine derivatives such as ethanolamine, dimethylformamide etc. Furthermore, it is also possible to mix the compounds and composition of the invention with various high molecular weight compounds and other auxiliary agents, particularly nonionic or ionic surfactants, sodium alginate, carboxymethylcellulose, methylcellulose, polyvinyl alcohol etc., which may be incorporated to improve the properties of the preparation and to enhance its activity towards the plant being treated. We prefer to blend from 0.1 to 100 parts by weight, more preferably from 0.5 to 20 parts by weight, of one or more of the synergistic agents of the invention with 1 part by weight of one or more gibberellins; however, the precise proportions employed are not limiting.

In the following Examples, various preparations for plant growth regulation are illustrated: all parts given are by weight.

EXAMPLE 12

Dust

1 Part of gibberellins, 5 parts of 3-methoxycarbonyl-2-methyl-1-(p-tolylcarbamoyl)-isourea (Compound 1), 47 parts of talc and 47 parts of clay were blended in a mixer and then powdered with a hammermill to give a dust.

EXAMPLE 13

Wettable Powder

5 Parts of gibberellins, 20 parts of 2-ethyl-3-methoxycarbonyl-1-(p-tolylcarbamoyl)-isourea (Compound 2), 54 parts of clay, 10 parts of diatomaceous earth, 5 parts of white carbon, 3 parts of sodium ligninsulphonate, 2 parts of Newcoal-1106 (a trade name for a surfactant of Nippon Nyukazai K.K., Japan) and 1 part of polyvinyl alcohol were blended homogeneously in a mixer and powdered three times in a hammermill to give a wettable powder.

EXAMPLE 14

Dust

1 Part of gibberellins, 5 parts of 1-isopropylcarbamoyl-3-methoxycarbonyl-2-propargylisothiourea (Compound 85), 47 parts of talc and 47 parts of clay were blended in a mixer and powdered with a hammermill to give a dust.

EXAMPLE 15

Wettable Powder

5 Parts of gibberellins, 20 parts of 2-allyl-1-isopropylcarbamoyl-3-methoxycarbonylisothiourea (Compound 84), 54 parts of clay, 10 parts of diatomaceous earth, 5 parts of white carbon (precipitated silica), 3 parts of sodium ligninsulphonate, 2 parts of Newcoal-1106 and 1 part of polyvinyl alcohol were blended homogeneously in a mixer and then powdered three times with a hammermill to give a wettable powder.

EXAMPLE 16

Dust

1 Part of gibberellins, 5 parts of 4-ethoxy-1,3-dihydro-1(p-tolyl)-1,3,5-triazine-2,6-dione (Compound 107), 47 parts of talc and 47 parts of clay were blended in a mixer and powdered with a hammermill to give a dust.

EXAMPLE 17

Wettable Powder

5 Parts of gibberellins, 20 parts of 1-(p-chlorophenyl)-4-ethoxy-1,3-dihydro-1,3,5-triazine-2,6-dione (Compound 108), 54 parts of clay, 10 parts of diatomaceous earth, 5 parts of white carbon, 3 parts of sodium ligninsulphonate, 2 parts of Newcoal-1106 and 1 part of polyvinyl alcohol were blended homogeneously in a mixer and powdered three times with a hammermill to give a wettable powder.

The preparation of the present invention may be applied to the plant to be treated by any of the following methods or any other method commonly used for the application of treatment agents to plants:

Diluting the preparation with water and sprinkling the resulting suspension over the whole body of the plant or over certain specific organs, such as the flower or fruit;

diluting the preparation with a liquid, e.g. water, and dipping the seeds or fruits of the plant in the resulting preparation before sowing or as the plant grows;

diluting the preparation and mixing it with the soil before sowing or during plant growth;

sprinkling the preparation in the form of a dust on the seeds before sowing or on the whole plant as the plant grows;

mixing the preparation in the form of a dust with the soil before sowing or whilst the plant grows.

The amount of the preparation of the invention to be applied will vary considerably depending upon the type of plant to be treated, the desired effect and the method of application. Where the preparation is to be sprinkled on the plant body for the purpose of plant growth regulation, we prefer to use a preparation containing from 10 to 1,000 ppm, preferably from 20 to 250 ppm, of the total of the synergistic agent and gibberellin and that the preparation should be used in such an amount that the whole of the body of the plant is adequately covered.

The synergistic effect of the synergistic agents of the invention is further illustrated by the following non-limiting Examples.

EXAMPLE 18

Measurement of Synergistic Effect on Growth of Rice Seeds

Into a tubular bottle of diameter 2.5 cm and height 6.0 cm was introduced 10 ml of a 0.5% agar solution containing a growth regulatory preparation (as defined hereafter) and the liquid was solidified in the bottle. 5 grains of germination-induced rice seed (Strain Kinmaze) were then sown in the bottle and the bottle was illuminated under a white fluorescent light of about 5000 lux at 30° C. After 4 days, the height of each rice plant was measured.

Each growth regulatory preparation tested contained one of the synergistic agents of the present invention listed in Table III and 10 ppm of gibberellins; they were prepared by producing a wettable powder following the procedure of Example 13, diluting this by 50% with water and then further diluting it to give the prescribed concentration of synergistic agent. Also, as controls, similar preparations containing the synergistic agent of the invention alone or gibberellin alone were employed. In each case, the synergistic agent of the invention was employed in an amount of 50 ppm (except for Compounds 29, 36, 45, 46, 112, 114 and 116 which were each employed in an amount of 10 ppm), and the gibberellins were employed in an amount of 10 ppm.

The synergistic effect was calculated from the following equation:

$$\text{Synergistic effect} \frac{[Am + G]}{[Am] + [G]} \times 100$$

where

[Am+G] represents the acceleration of plant growth, compared with a control, caused by the preparation containing both the synergistic agent of the invention and gibberellins;

[Am] represents the acceleration of plant growth, compared with a control, caused by the application of gibberellin alone;

[G] represents the acceleration of plant growth, caused by the application of the synergistic agent of the present invention.

In each case, the acceleration of plant growth was determined by measuring the height of the plants and comparing with a control to which no plant growth regulator had been applied.

The results are summarized in following Table III, in which the synergistic effect as determined by the above equation is summarized as follows:

| | |
|---|---|
| not more than 84 | — |
| 85–115 | 0 |
| 116–135 | 1 |
| 136–155 | 2 |
| 156–175 | 3 |
| 176–195 | 4 |
| not less than 196 | 5. |

TABLE III

| Compound No. | Synergistic effect |
|---|---|
| 1 | 4 |
| 2 | 5 |
| 3 | 4 |
| 4 | 4 |
| 5 | 4 |
| 6 | 5 |
| 7 | 5 |
| 8 | 3 |
| 9 | 2 |
| 10 | 4 |
| 11 | 4 |
| 12 | 4 |
| 13 | 5 |
| 14 | 5 |
| 15 | 4 |
| 16 | 5 |
| 17 | 4 |
| 18 | 3 |
| 19 | 5 |
| 20 | 5 |
| 21 | 3 |
| 22 | 3 |
| 23 | 2 |
| 24 | 1 |
| 25 | 2 |
| 26 | 3 |
| 27 | 3 |
| 28 | 1 |
| 29 | 2 |
| 30 | 2 |
| 31 | 3 |
| 32 | 4 |
| 33 | 5 |
| 34 | 1 |
| 35 | 2 |
| 36 | 3 |
| 37 | 1 |
| 38 | 3 |
| 39 | 2 |
| 40 | 4 |
| 41 | 1 |
| 42 | 3 |
| 43 | 3 |
| 44 | 1 |
| 45 | 3 |
| 46 | 1 |
| 47 | 3 |
| 48 | 3 |
| 49 | 4 |
| 50 | 1 |
| 51 | 3 |
| 52 | 3 |
| 53 | 3 |
| 54 | 3 |
| 55 | 5 |
| 56 | 4 |
| 57 | 3 |
| 58 | 3 |
| 59 | 1 |
| 60 | 3 |
| 61 | 2 |
| 62 | 2 |
| 63 | 3 |
| 64 | 5 |
| 65 | 3 |
| 66 | 5 |
| 67 | 3 |
| 68 | 5 |
| 69 | 2 |
| 70 | 5 |
| 71 | 5 |
| 72 | 5 |
| 73 | 5 |
| 74 | 1 |
| 75 | 3 |
| 76 | 1 |
| 77 | 1 |
| 78 | 1 |
| 79 | 1 |
| 80 | 3 |
| 81 | 1 |
| 84 | 1 |
| 85 | 1 |
| 86 | 1 |
| 87 | 0 |
| 88 | 1 |
| 89 | 0 |
| 90 | 0 |
| 91 | 1 |
| 92 | 3 |
| 93 | 1 |
| 94 | 1 |
| 95 | 1 |
| 96 | 2 |
| 97 | 1 |
| 106 | 2 |
| 107 | 5 |
| 108 | 4 |
| 109 | 4 |
| 110 | 4 |
| 111 | 2 |
| 112 | 1 |
| 113 | 4 |
| 114 | 4 |
| 115 | 1 |
| 116 | 3 |
| 117 | 2 |
| 118 | 2 |
| 119 | 1 |
| 120 | 3 |
| 121 | 1 |
| 122 | 4 |
| 123 | 4 |
| 124 | 4 |
| 125 | 2 |
| 126 | 1 |
| 127 | 2 |
| 128 | 3 |
| 129 | 1 |
| 130 | 2 |
| 131 | 2 |
| 132 | 4 |
| 133 | 4 |

EXAMPLE 19

Effect on Height of Rice Plants

Wettable powders containing either gibberellins alone, Compound 4 alone or a mixture of Compound 4 with gibberellins were prepared according to the procedure described in Example 13 and were diluted to 50% with water and then further diluted to give the concentration of active ingredients shown in Table IV. The gibberellins employed were produced by Wako Junyakukogyo Kabushiki Gaisha, Japan.

2 ml of the resulting liquid preparation were introduced into a tubular bottle of diameter 2.5 cm and height 6.0 cm and then 5 grains of a germination-induced seed (Strain Kinmaze) were sown thereon. The seeds were then placed under a white fluorescent light of about 4000 lux for 4 days, after which the height of each rice plant was measured. The results are shown in Table IV, which also shows the results obtained when water alone was employed instead of the liquid preparation described above.

TABLE IV

| Cpd 4 Amount (ppm) | Gibberellins Amount (ppm) | Height of Plant (mm) | Height difference from Control (mm) |
|---|---|---|---|
| —(Control) | — | 26.1 | — |
| — | 1 | 33.6 | 7.5 |
| — | 10 | 48.2 | 22.1 |
| 10 | — | 36.2 | 10.1 |
| 10 | 1 | 50.2 | 24.1 |
| 10 | 10 | 68.7 | 42.6 |
| 50 | — | 40.3 | 14.2 |
| 50 | 1 | 67.8 | 41.7 |
| 50 | 10 | 94.6 | 68.5 |

EXAMPLE 20

Effect on Height of Rice Plants

The procedure described in Example 19 was repeated, and the height of the plants was measured after 4 or 6 days. The results are shown in Table V.

TABLE V

| Cpd 4 Amount (ppm) | Gibberellins Amount (ppm) | Height of Plant (mm) | | Height difference from Control (mm) | |
|---|---|---|---|---|---|
| | | 4 days | 6 days | 4 days | 6 days |
| —(Control) | — | 30.7 | 41.0 | — | — |
| 50 | — | 42.9 | 55.7 | 12.2 | 14.7 |
| — | 10 | 50.9 | 99.2 | 20.2 | 58.2 |
| 50 | 10 | 101.0 | 180.0 | 70.3 | 139.0 |

EXAMPLE 21

Effect on Height of Rice Plants

The procedure described in Example 19 was repeated, except that Compound 4 was replaced by Compound 75. The results are shown in Table VI.

TABLE VI

| Cpd 75 Amount (ppm) | Gibberellins Amount (ppm) | Height of Plant (mm) | Height difference from Control (mm) |
|---|---|---|---|
| —(Control) | — | 24.3 | — |
| — | 1 | 32.0 | 7.7 |
| — | 10 | 39.1 | 14.8 |
| 10 | — | 29.0 | 4.7 |
| 10 | 1 | 45.1 | 20.8 |
| 10 | 10 | 52.0 | 27.7 |
| 50 | — | 30.6 | 6.3 |
| 50 | 1 | 50.9 | 26.6 |
| 50 | 10 | 60.1 | 35.8 |

EXAMPLE 22

Effect on Height of Rice Plants

The procedure of Example 21 was repeated, the height of the plants being measured after 4 and 6 days. The results are shown in Table VII.

TABLE VII

| Cpd 75 Amount (ppm) | Gibberellins Amount (ppm) | Height of Plant (mm) | | Height difference from Control (mm) | |
|---|---|---|---|---|---|
| | | 4 days | 6 days | 4 days | 6 days |
| —(Control) | — | 24.5 | 48.7 | — | — |
| 50 | — | 30.6 | 55.0 | 6.1 | 6.3 |
| — | 10 | 38.0 | 104 | 13.5 | 55.3 |
| 50 | 10 | 59.4 | 152 | 34.9 | 103.3 |

EXAMPLE 23

Effect on Height of Rice Plants

The procedure described in Example 19 was repeated, except that Compound 107 was used in place of Compound 4. The results are shown in following Table VIII.

TABLE VIII

| Cpd 107 Amount (ppm) | Gibberellins Amount (ppm) | Height of Plant (mm) | Height difference from Control (mm) |
|---|---|---|---|
| —(Control) | — | 28.9 | — |
| — | 1 | 44.9 | 16.0 |
| — | 10 | 51.5 | 22.6 |
| 10 | — | 31.8 | 2.9 |
| 10 | 1 | 58.8 | 29.9 |
| 10 | 10 | 69.3 | 40.4 |
| 50 | — | 42.8 | 13.9 |
| 50 | 1 | 67.2 | 38.3 |
| 50 | 10 | 101 | 72.1 |

EXAMPLE 24

Effect on Height of Rice Plants

The procedure described in Example 23 was repeated, the height of the plants being measured after 4 and 6 days. The results are shown in Table IX.

TABLE IX

| Cpd 107 Amount (ppm) | Gibberellins Amount (ppm) | Height of Plant (mm) | | Height difference from Control (mm) | |
|---|---|---|---|---|---|
| | | 4 days | 6 days | 4 days | 6 days |
| —(Control) | — | 28.9 | 48.7 | — | — |
| 50 | — | 39.4 | 60.1 | 10.5 | 11.4 |
| — | 10 | 52.4 | 104 | 23.5 | 55.3 |
| 50 | 10 | 95.2 | 177 | 66.3 | 128.3 |

EXAMPLE 25

Effect on Flower Formation of Young Japanese Cypress Plants

Test preparations were prepared by: preparing a wettable powder containing gibberellins and/or Compound 13, substantially as described in Example 13; diluting those wettable powders to produce the concentration of active ingredients shown in Table X; and adding a spreader sold under the trade name Shingramin by Sankyo Company, Limited at a concentration of 0.03%.

The resulting preparations were then sprayed onto two year old Japanese cypress [*Chamaecyparis obtusa* (Sieb. et Zucc.) Endl.] plants produced from cuttings on Aug. 13 and Aug. 20, 1975, five plants being used in this test. On May 27, 1976, ten branches of each cypress were investigated to count the numbers of branches bearing male flowers of said cypress and the respective numbers so counted were divided by the investigated number (ten). Then, an average was taken on a total of five plants, which is shown in Table X as "average number of flowering branches". As a control, the experiment was repeated except that the gibberellins and Compound 13 were omitted; the results are also shown in Table X.

TABLE X

| Cpd 13 Amount (ppm) | Gibberellins Amount (ppm) | Average number of flowering branches | |
|---|---|---|---|
| | | Male Flowers | Female Flowers |
| —(Control) | — | 0.2 | 0.2 |
| — | 300 | 0.2 | 0 |
| 200 | — | 0 | 0 |
| 200 | 300 | 6.0 | 1.6 |

It is clear from the Table that the combined use of Compound 13 with gibberellins has a remarkable effect on flower formation.

We claim:

1. A process for the treatment of a plant by the administration in the presence of at least one gibberellin of a growth-stimulating effective amount of a synergistic agent selected from the group consisting of: compounds having the formula (I):

$$R^1O-\overset{O}{\underset{\|}{C}}-N=\overset{XR^2}{\underset{|}{C}}-NH-\overset{O}{\underset{\|}{C}}-NHR^3 \quad (I)$$

wherein:
R$^1$ represents a hydrogen atom or a lower alkyl group, a lower alkenyl group, a lower alkynyl group or a phenyl group;
R$^2$ represents a lower alkyl group, a lower alkenyl group, a lower alkynyl group or a benzyl group;
R$^3$ represents a lower alkyl group, a cyclohexyl group or a group of the formula:

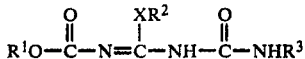

in which R$^4$ represents a lower alkyl group, a lower alkoxy group or a halogen atom and n is 0, 1, 2 or 3; and
X represents an oxygen or a sulphur atom.

2. The process of claim 1 wherein said plant produces no or substantially no gibberellins and said synergistic agent is administered in association with at least one gibberellin.

3. The process of claim 1 wherein said plant naturally produces gibberellins and said synergistic agent is administered without additional gibberellin.

4. The process of claim 1 wherein: R$^1$ represents a straight chain or branched chain lower alkyl group having from 1 to 4 carbon atoms, a straight chain or branched chain lower alkenyl group having 3 or 4 carbon atoms or a straight chain or branched chain alkynyl group having 3 or 4 carbon atoms; R$^2$ represents a straight chain or branched chain lower alkyl group having from 1 to 4 carbon atoms, a straight chain or branched chain lower alkenyl group having 3 or 4 carbon atoms or a straight chain or branched chain lower alkynyl group having 3 or 4 carbon atoms; and R$^3$ represents a straight chain or branched chain alkyl group having from 3 to 6 carbon atoms or a group of formula:

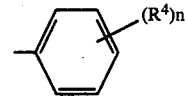

in which R$^4$ represents a methyl group, a methoxy group or a halogen atom and n is 0, 1, 2 or 3.

5. The process of claim 4 wherein R$^3$ represents a p-chlorophenyl group, a p-bromophenyl group, a p-iodophenyl group, a p-methylphenyl group, a p-ethylphenyl group, a 2,4-dichlorophenyl group, a 2,4-dimethylphenyl group or a 4-chloro-2-methylphenyl group.

6. A composition for the treatment of plants comprising at least one gibberellin and a growth-stimulating effective amount of at least one synergistic agent selected from the group consisting of compounds of formula (I):

$$R^1O-\overset{O}{\underset{\|}{C}}-N=\overset{XR^2}{\underset{|}{C}}-NH-\overset{O}{\underset{\|}{C}}-NHR^3 \quad (I)$$

wherein:
R$^1$ represents a hydrogen atom or a lower alkyl group, a lower alkenyl group, a lower alkynyl group or a phenyl group;
R$^2$ represents a lower alkyl group, a lower alkenyl group, a lower alkynyl group or a benzyl group;
R$^3$ represents a lower alkyl group, a cyclohexyl group or a group of the formula:

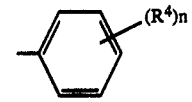

in which R$^4$ represents a lower alkyl group, a lower alkoxy group or a halogen atom and n is 0, 1, 2 or 3; and
X represents an oxygen or a sulphur atom.

7. The composition of claim 6 wherein: R$^1$ represents a straight chain or branched chain lower alkyl group having from 1 to 4 carbon atoms, a straight chain or branched chain lower alkenyl group having 3 or 4 carbon atoms or a straight chain or branched chain alkynyl group having 3 or 4 carbon atoms; R$^2$ represents a straight chain or branched chain lower alkyl group having from 1 to 4 carbon atoms, a straight chain or branched chain lower alkenyl group having 3 or 4 carbon atoms or a straight chain or branched chain lower alkynyl group having 3 or 4 carbon atoms; and R$^3$ represents a straight chain or branched chain alkyl group having from 3 to 6 carbon atoms or a group of formula:

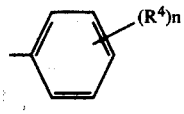

in which R⁴ represents a methyl group, a methoxy group or a halogen atom and n is 0, 1, 2 or 3.

8. The composition of claim 7 wherein $R^3$ represents a p-chlorophenyl group, a p-bromophenyl group, a p-indophenyl group, a p-methylphenyl group, a p-ethyl- phenyl group, a 2,4-dichlorophenyl group, a 2,4-dimethylphenyl group or a 4-chloro-2-methylphenyl group.

9. The composition of claim 6 wherein said synergistic agent is employed in an amount of from 0.1 to 100 parts by weight per part by weight of gibberellins.

10. The composition of claim 6 in the form of an agriculturally administrable composition selected from the group consisting of dusts, granules, grains, wettable powders, emulsions and aqueous solutions.

11. The composition of claim 10 which additionally comprises an adjuvant selected from the group consisting of solid carriers, liquid carriers, high molecular weight compounds, non-ionic and ionic surfactants, sodium alginate, carboxymethylcellulose, methylcellulose and polyvinyl alcohol.

* * * * *

UNITED STATES PATENT AND TRADEMARK OFFICE
CERTIFICATE OF CORRECTION

PATENT NO. : 4,406,687

DATED : Sept. 27, 1983

INVENTOR(S) : Kozo Oyamada, et al

It is certified that error appears in the above-identified patent and that said Letters Patent is hereby corrected as shown below:

```
In the heading of the Patent [30] should read as
follows:

[30]      Foreign Application Priority Data

Jul. 16, 1975 [JP]    Japan.............. 46-87030
   Sep.  5, 1975 [JP]    Japan..............50-107823
   Sep. 22, 1975 [JP]    Japan..............50-114473
```

*Signed and Sealed this*

*Twenty-seventh* Day of *March 1984*

[SEAL]

*Attest:*

GERALD J. MOSSINGHOFF

*Attesting Officer*     *Commissioner of Patents and Trademarks*